(12) United States Patent
Shankar et al.

(10) Patent No.: US 11,077,103 B2
(45) Date of Patent: Aug. 3, 2021

(54) NALOXEGOL OXALATE AND SOLID DISPERSION THEREOF

(71) Applicants: AUROBINDO PHARMA LIMITED, Hyderabad (IN); Rama Shankar, Hyderabad (IN); Nimesh Chandra Misra, Hyderabad (IN); Siva Rama Kasibabu Velegula, Hyderabad (IN); Suresh Chapala, Hyderabad (IN); Sivakumaran Meenakshisunderam, Hyderabad (IN)

(72) Inventors: Rama Shankar, Hyderabad (IN); Nimesh Chandra Misra, Hyderabad (IN); Siva Rama Kasibabu Velegula, Hyderabad (IN); Suresh Chapala, Hyderabad (IN); Sivakumaran Meenakshisunderam, Hyderabad (IN)

(73) Assignee: Aurobindo Pharma Ltd., Hyderabad (IN)

( * ) Notice: Subject to any disclaimer, the term of this patent is extended or adjusted under 35 U.S.C. 154(b) by 47 days.

(21) Appl. No.: 16/462,856

(22) PCT Filed: Nov. 22, 2017

(86) PCT No.: PCT/IB2017/057325
§ 371 (c)(1),
(2) Date: May 21, 2019

(87) PCT Pub. No.: WO2018/096464
PCT Pub. Date: May 31, 2018

(65) Prior Publication Data
US 2020/0253955 A1 Aug. 13, 2020

(30) Foreign Application Priority Data

Nov. 23, 2016 (IN) .............................. 201641036692
Jun. 30, 2017 (IN) .............................. 201741022942

(51) Int. Cl.
*A61K 31/485* (2006.01)

(52) U.S. Cl.
CPC .................................. *A61K 31/485* (2013.01)

(58) Field of Classification Search
CPC .... A61K 31/485; A61K 31/765; A61K 9/146; A61K 9/1635; A61P 25/04; C08G 65/33306; C07D 489/08
See application file for complete search history.

(56) References Cited

U.S. PATENT DOCUMENTS

2007/0082919 A1* 4/2007 Barrett ...................... A61P 1/04
514/263.36

FOREIGN PATENT DOCUMENTS

EP         3228307 A1 * 10/2017   ........... A61K 31/485
WO    WO-2012044243 A1 *  4/2012   .............. A61P 39/00

* cited by examiner

*Primary Examiner* — Sarah Pihonak
(74) *Attorney, Agent, or Firm* — Jay R Akhave (57) ABSTRACT

The present invention relates to solid dispersion of Naloxegol oxalate. Further, the present invention relates to an improved process for Naloxegol oxalate and intermediates thereof.

5 Claims, 3 Drawing Sheets

NALOXEGOL OXALATE AND SOLID DISPERSION THEREOF

FIELD OF THE INVENTION

The present invention relates to solid dispersion of Naloxegol oxalate. Further, the present invention relates to a process for Naloxegol oxalate and intermediates thereof.

BACKGROUND OF THE INVENTION

Naloxegol is a PEGylated derivative of Naloxone. Naloxegol oxalate, chemically known as (5α,6α)-17-allyl-6-(2,5, 8,11,14,17,20 heptaoxadocosan-22-yloxy)-4,5-epoxymorphinan-3,14-diol oxalate and has a structure of formula I:

I

Naloxegol, which is marketed in the form of its oxalate salt is an opioid antagonist drug approved in United States and several other countries under the trade name MOVANTIK®. Naloxegol oxalate is used in the treatment of opioid-induced constipation (OIC) in adult patients with chronic non-cancer pain.

U.S. Pat. No. 7,786,133 discloses Naloxegol and its pharmaceutically acceptable salts generically, and U.S. Pat. No. 9,012,469 discloses specifically Naloxegol oxalate and process for preparation thereof.

U.S. Pat. No. 9,012,469 describes crystalline Form A and Form B of Naloxegol oxalate and process for the preparation thereof.

The occurrences of different solid forms are possible for some compounds. A single compound may exist in different solid forms. Various solid forms of a drug substance can have different chemical and physical properties, including melting point, chemical reactivity, apparent solubility, dissolution rate, optical and mechanical properties, vapor pressure, and density. These properties can have a direct effect on the ability to process and/or manufacture the drug substance and the drug product, as well as on drug product stability, dissolution, and bioavailability. Thus, solid forms can affect the quality, safety, and efficacy of the drug product, regulatory authorities require that efforts shall be made to identify all solid forms, e.g., crystalline, amorphous, solvated, etc., of drug substances.

Therefore, there is a need to develop amorphous Naloxegol oxalate, which is stable, pure and industrially scalable.

U.S. Pat. No. 8,183,376 discloses a process for converting 3-O-MEM-Naloxone to 3-O-MEM α-Naloxol by stereoselective reduction using potassium tri sec.-butylborohydride in presence of THF.

U.S. Pat. No. 7,786,133 discloses a process for preparing Naloxegol. The process is depicted in the scheme-I:

Naloxegol + β-epimer

Chromatographic Separation using silica gel column

I

Naloxegol

The present inventors observed that the process of prior art gives 3-O-MEM-Naloxone as thick viscous liquid which contains un-reacted reagents of the process as well as the process impurity, 3,14-di-O-MEM Naloxone:

These impurities are carried forward in subsequent steps to Naloxegol. These impurities generated during preparation of intermediates are undesirable and requires tedious purification processes, for example, column chromatography, at Naloxegol base.

Therefore, there is a need to develop an improved process for Naloxegol, which involves isolation of MEM-Naloxone and 3-O-MEM α-Naloxol or a pharmaceutically acceptable salt thereof in solid form, and involves selective purification for 3-O-MEM Naloxegol and Naloxegol to obtain pure Naloxegol Oxalate.

OBJECTIVE OF THE INVENTION

An objective of the present invention is to provide a solid dispersion of Naloxegol oxalate and an improved process for preparation of Naloxegol oxalate.

SUMMARY OF THE INVENTION

In an aspect, the present invention provides a solid dispersion of Naloxegol oxalate comprising Naloxegol oxalate in an amorphous and at least one pharmaceutically acceptable carrier.

In another aspect, the present invention provides a process for the preparation solid dispersion of Naloxegol oxalate, which comprises:
  a) providing a solution of dissolving Naloxegol oxalate in a solvent;
  b) adding a pharmaceutically acceptable excipient; and
  c) isolating amorphous solid dispersion of Naloxegol oxalate.

In another aspect, the present invention provides a process for the purification of 3-O-MEM α-Naloxone, which comprises treatment of 3-O-MEM-Naloxone with a base; and optionally isolating the solid of 3-O-MEM-Naloxone having purity greater than 99% by HPLC.

In another aspect, the present invention provides a process for the preparation of 3-O-MEM α-Naloxol, which comprises stereoselective reduction of 3-O-MEM naloxone or salt thereof, with reducing agent in presence of an additive and a solvent to provide 3-O-MEM α-Naloxol having α-epimer purity is greater than 99.7%.

In another aspect, the present invention provides a process for the purification of 3-O-MEM α-Naloxol or salt thereof, which comprises:
a) treatment of 3-O-MEM α-Naloxol with an acid in a solvent to provide acid addition salt of 3-O MEM; and
b) optionally, isolating the salt of 3-O-MEM α-Naloxol; and
c) treatment of the acid addition salt of 3-O-MEM α-Naloxol with a base to provide 3-O-MEM α-Naloxol.

In another aspect, the present invention provides solid form of 3-O-MEM α-Naloxol salt of formula II and 3-O-MEM Naloxone of Formula III:

Formula II

Formula III

In another aspect, the present invention provides a process for the purification of 3-O-MEM naloxegol having purity greater than or equal to 95.5%, which comprises:
i) treating 3-O-MEM naloxegol with an acid to provide acid addition salt of 3-O-MEM naloxegol;
ii) optionally isolating the acid addition salt of step (i);
iii) treating the acid addition salt of 3-O-MEM naloxegol with a base to provide 3-O-MEM naloxegol;
iv) optionally, isolating 3-O-MEM naloxegol.

In another aspect, the present invention provides a process for the purification of Naloxegol or salt thereof, which comprises:
i) treating Naloxegol with an acid to provide acid addition salt of naloxegol;
ii) optionally, isolating the acid addition salt of Naloxegol;
iii) treating the acid addition salt of Naloxegol with a base to provide pure Naloxegol or salt thereof.

In another aspect of the present invention, there is provided a process for the preparation of compound of formula A:

Formula A wherein X is leaving group such as mesyl, tosyl, halo, nosyl
which comprises:
a) condensation of triethyleneglycol monomethylether monomesylate with tetraethylene glycolmonobenzyl ether to provide heptaethylene glycol benzyl methyl ether;
b) conversion of the heptaethylene glycol benzyl methyl ether to compound of formula A.

DETAILED DESCRIPTION OF THE INVENTION

The "pure" of the present invention refers to, unless specified otherwise, that the compounds or salts thereof are having purity greater than about than about 98.0% or greater than about 99.5% by HPLC. Further, the "pure" refers to the material of present invention is substantially free from impurities i.e. the impurities are less than about 1% or less than about 0.6% or less than about 0.3% by HPLC analysis.

Furthermore, the present invention refers to "pharmaceutically acceptable salt" or "salt" or "HX" that may be obtained from inorganic acid or organic acid. The inorganic acid is selected from hydrochloric acid, hydrobromic acid, sulfuric acid, phosphoric acid and the like; the organic acid may be selected from oxalic acid, acetic acid, maleic acid, succinic acid, methane sulfonic acid and the like, preferably the acid is oxalic acid.

The pure amorphous Naloxegol oxalate of the present invention have a superior polymorphic purity is evident from perfect a single broad diffraction peak (halo) in XRPD.

The amorphous of the present invention may have a chemical purity by High Performance Liquid Chromatography (HPLC) of greater than about 96.0% or greater than about 98.0% or greater than about 99.0% or greater than about 99.5%. The amorphous Naloxegol oxalate of the present invention may have residual solvents content within the ICH guidelines.

The solid state of the present invention means, unless specified otherwise, that the compounds or salts thereof are isolated as solid. The solid state can be in the crystalline, partially crystalline or amorphous.

The solvents referred in the present invention refers, unless otherwise defined, alcoholic solvents such as methanol, ethanol, n-propanol, isopropanol (2-propanol), n-butanol, isobutanol, and t-butanol; ketones such as acetone, propanone, and 2-butanone; esters such as ethyl acetate, n-propyl acetate, isopropylacetate and n-butyl acetate and the like; ethers such as dimethylether, diethylether, methyl-tertiarybutylether, ethylmethylether, diisopropylether, tetrahydrofuran, and dioxane; halogenated solvents such as dichloromethane, 1,2-dichloroethane and chloroform; hydrocarbons such as toluene, xylene, cyclohexane, n-hexane, and n-heptane; nitrile solvents such as acetonitrile, and propionitrile; aprotic polar solvents, such as N, N-dimethylformide (DMF), Dimethylsulfoxide (DMSO), and N, N-dimethylacetamide (DMA) or mixtures thereof.

In an aspect, the present invention provides a solid dispersion of Naloxegol oxalate comprising Naloxegol oxalate in an amorphous and at least one pharmaceutically acceptable carrier.

Figure 1:
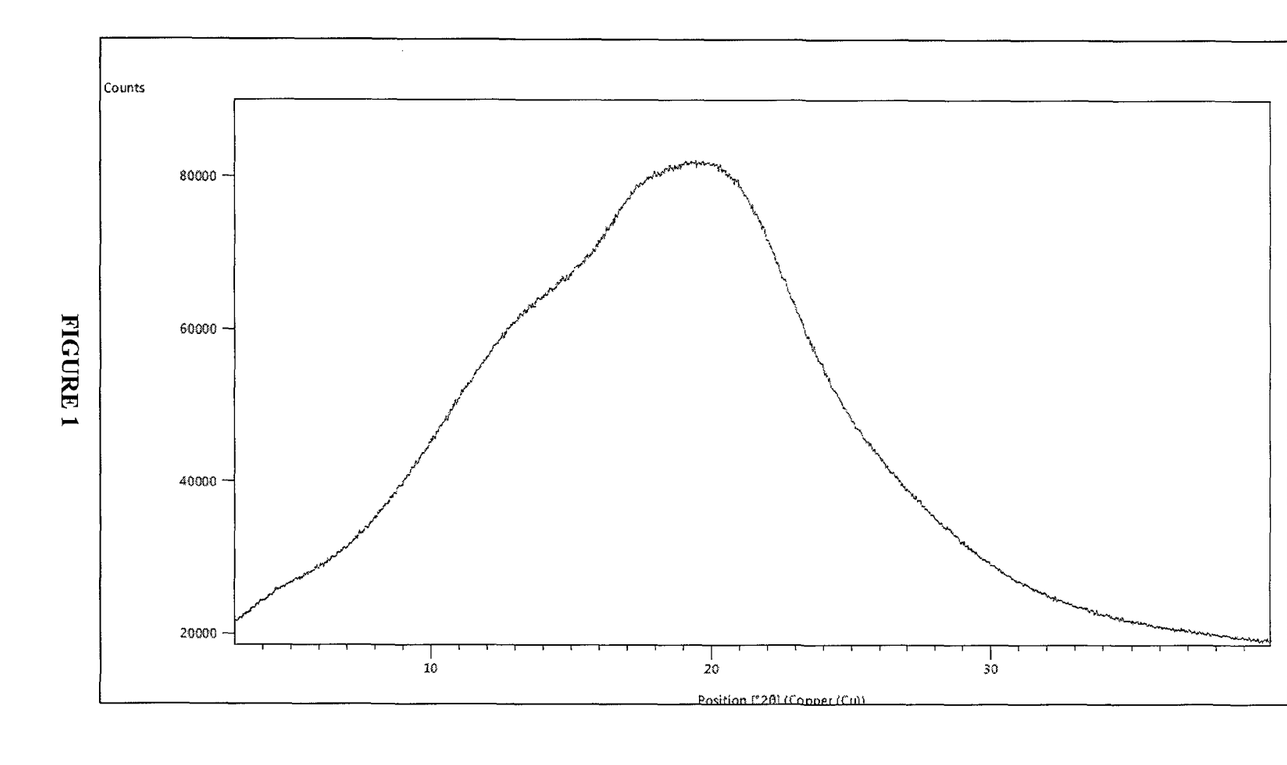
FIG. 1 is X-ray power diffraction ("XRPD") pattern of solid dispersion of Naloxegol oxalate prepared according to the present invention.

The solid dispersion is characterized by X-ray powder diffraction pattern, which is depicted in FIG. 1.

In another aspect, the present invention provides a process for the preparation solid dispersion of Naloxegol oxalate, which comprises:
a) dissolving Naloxegol oxalate in a solvent to form a solution;
b) adding a pharmaceutically acceptable excipient; and
c) isolating amorphous solid dispersion of Naloxegol oxalate.

The solution of Naloxegol Oxalate in step (a) may be provided either by dissolving Naloxegol Oxalate in a suitable solvent or it may be provided directly from a reaction mixture containing it that is obtained during the course of its manufacture. Suitable solvent that may be used in step a) may be selected from water; various classes of solvents, such as for example, alcoholic solvents, ketones, esters, ethers, halogenated, hydrocarbons, nitrile, aprotic polar solvents, or mixtures thereof.

The pharmaceutically acceptable carrier may be added to a reaction solution containing Naloxegol oxalate to provide solution, dispersion or suspension. The solvent(s) for providing the solution, suspension or dispersion of Naloxegol oxalate along with one or more pharmaceutically acceptable carriers in step b) may be selected from the above list mentioned for providing solution.

Suitable Pharmaceutically acceptable carriers that may be used in step b) include, but not restricted to water soluble as well as water insoluble carriers. The carriers are polyvinylpyrrolidone (povidone), copovidone, polyvinyl alcohol, hydroxypropyl methylcellulose (hypromellose; HPMC), hydroxypropylcellulose (HPC), polyvinyl caprolactam-polyvinyl acetate-polyethylene glycol graft co-polymer, methylcellulose, ethylcellulose, hydroxypropyl cellulose and its derivatives, microcrystalline celluloses, polymethacrylates, hypromellose phthalate, hypromellose acetate succinate, cellulose acetate phthalate, carboxymethyl ethyl cellulose and crospovidone. The preferable pharmaceutically acceptable carriers are povidone K-30, Copovidone, HPC and HPMC.

The isolation may be obtained by techniques known in the art such as distillation, evaporation, oven drying, tray drying, spray drying, freeze-drying (lyophilization), fluid bed drying, flash drying, spin flash drying and agitated thin film dryer (ATFD), hot melt extrusion and the like. Particularly, the solution of step b) is lyophilized to obtain amorphous solid dispersion.

In another aspect, the present invention provides a process for the purification of 3-O-MEM α-Naloxone, which comprises treatment of 3-O-MEM-Naloxone with a base; and optionally isolating the solid of 3-O-MEM-Naloxone having purity 99% by HPLC.

The base is selected from inorganic base such as sodium hydroxide, lithium hydroxide, barium hydroxide, barium carbonate, potassium hydroxide, sodium carbonate, potassium carbonate, sodium hydride and the like or organic base such as diethyl amine, triethyl amine, diisopropyl amine, diisopropyl ethyl amine, N-methyl pyrrolidine, pyridine, and the like.

After treatment of 3-O-MEM-Naloxone with a base, the reaction mixture may be extracted into organic solvent and then isolated solid by concentrated, slurry in solvent or both. The solvent is hydrocarbon, for example, cyclohexane. The purity of 3-O-MEM-Naloxone is greater than or equal to 99%, preferably greater than about 99.5% by HPLC.

In another aspect, the present invention provides a process for the preparation of 3-O-MEM α-Naloxol or a pharmaceutically acceptable salt thereof, which comprises stereo selective reduction of 3-O-MEM naloxone or a salt thereof with reducing agent in presence of solvent and additive to provide 3-O-MEM α-Naloxol having α-epimer purity is greater than about 99.7%.

The present inventors found that the use of small amount of additive such as 2-Methoxyethanol during reduction unexpectedly improves the α/β ratio in the range of about 99:1 to 100:0 or to about 99:1 to 99.6:0.4.

The structure of β-epimer of 3-O-MEM Naloxol is:

The reducing agent for stereo selective reduction includes but not limited to Lithium tri-tert-butoxy aluminium hydride (LTBA). The solvent used for the selective reduction may be a alcohol, ether, hydrocarbon, and combinations thereof, an aprotic solvent, or a combination thereof. The temperature used for the reduction is about −20 to 50° C. over a period of about 15 minutes to about 1 hour or more. In an embodiment, the temperature used for the addition is about −15 to about 10° C.

The resultant 3-O-MEM α-Naloxol or a pharmaceutically acceptable salt thereof having α-epimer purity is greater than or equal to 99.7% by HPLC.

In another aspect, the present invention provides a process for the purification of 3-O-MEM α-Naloxol or salt thereof, which comprises:
a) treatment of 3-O-MEM α-Naloxol with an acid in a solvent to provide acid addition salt of 3-O MEM α-Naloxol having purity greater than or equal to 99.5%; and
b) optionally, isolating the salt of 3-O MEM α-Naloxol; and
c) treatment of the acid addition salt of 3-O-MEM α-Naloxol with a base to provide —O-MEM α-Naloxol.

The acid is selected from inorganic acid or organic acid. The inorganic acid/organic acids are defined above, preferably, the acid is oxalic acid. The solvent used for step a) is selected from alcohol, ester, ether, nitrile solvent or a combination thereof, preferably alcohol.

The isolation of salt may be performed using suitable techniques such as addition of anti-solvent, concentration, spray drying and the like. Particularly, the solid is precipitated by the addition of ether solvent such as methyl t-butyl ether. The resultant solid may be dried under vacuum at 10 to 50° C.

Further, the inventors of the present invention surprisingly found that pharmaceutically acceptable salt of 3-O-MEM

α-Naloxol and its isolation as solid improved the purity and reduced the content of impurities at greater level. The β-epimer content and other impurities are reduced to less than about 1% or less than about 0.5% or less than about 0.3% through formation of pharmaceutically acceptable salt of 3-O-MEM α-Naloxol.

The solid of 3-O-MEM-Naloxone and acid addition salt of 3-O-MEM α-Naloxol may be crystalline or amorphous, which are distinct from the prior art i.e. thick liquid or oily mass. Thus, these have different properties that make it particularly useful as intermediates for the preparation of Naloxegol oxalate. The properties are X-ray powder diffraction (XRPD) pattern, purity by HPLC, Differential Scanning Calorimetry (DSC) and thermogravimetric analysis ("TGA") curve.

Figure 2:
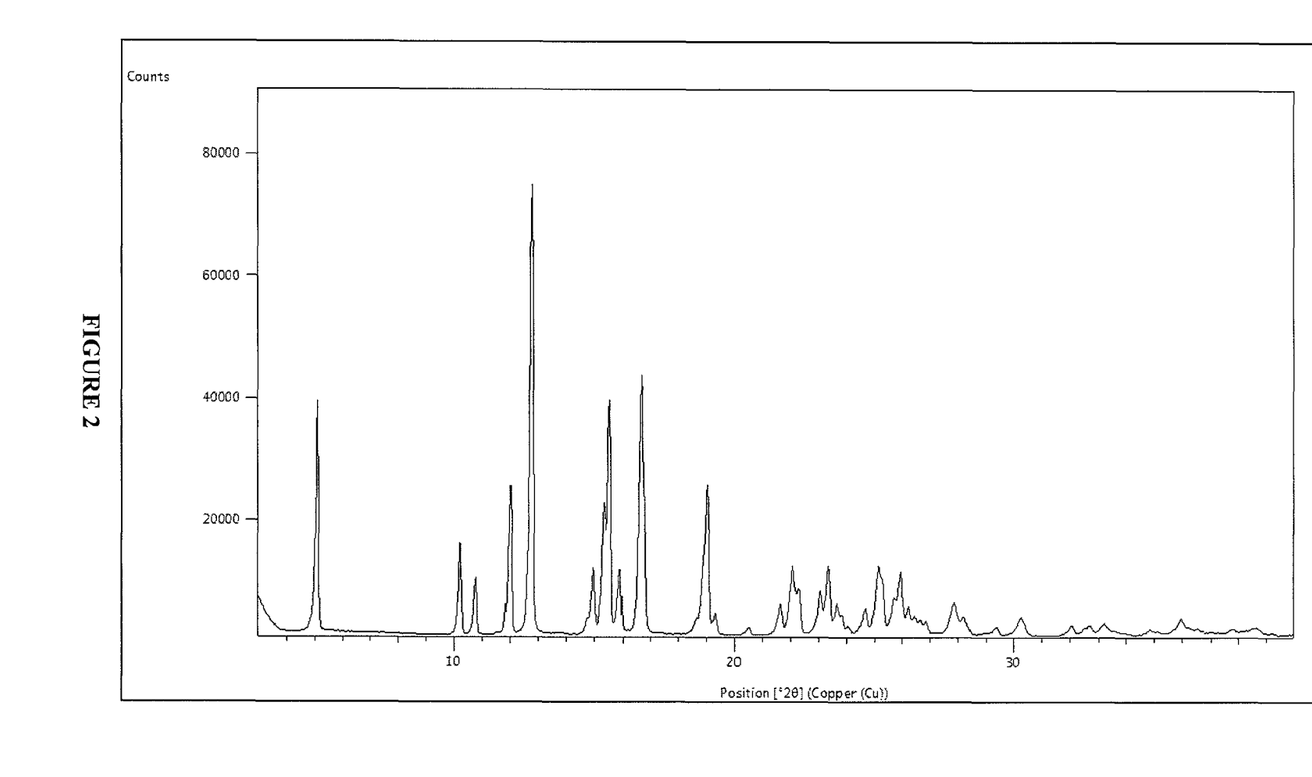
FIG. 2 is X-ray powder diffraction ("XRPD") pattern of 3-O-MEM Naloxone prepared according to example 3.
Figure 3:
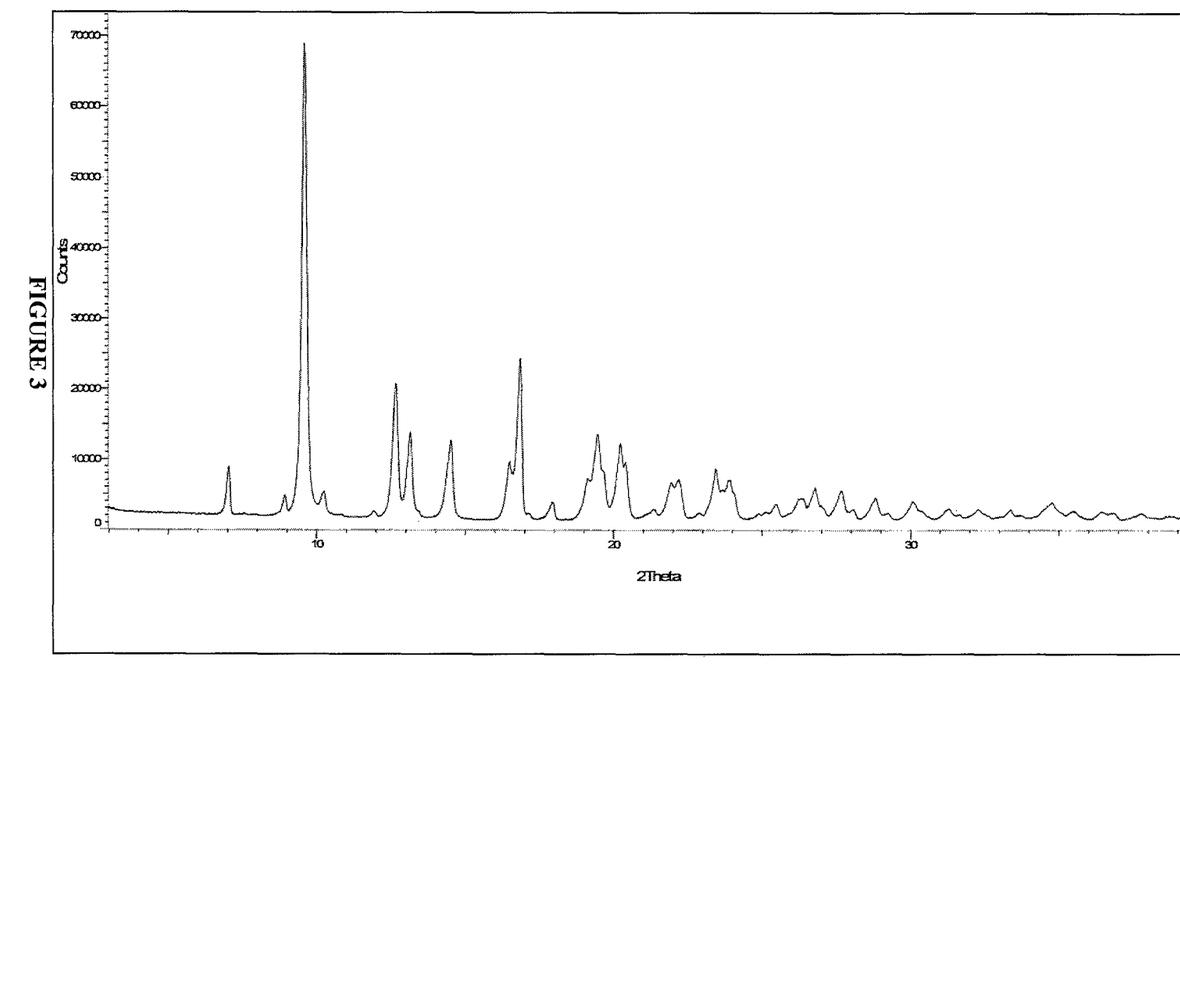
FIG. 3 is X-ray powder diffraction ("XRPD") pattern of 3-O-MEM α-Naloxol oxalate prepared according to example 5.

The XRD pattern of 3-O-MEM-Naloxone of the present invention is shown in FIG. 2. The XRD pattern of 3-O-MEM α-Naloxol oxalate of the present invention is shown in FIG. 3.

In another embodiment, 3-O-MEM-Naloxone and 3-O-MEM α-Naloxol or a pharmaceutically acceptable salt thereof of the present invention may be converted to naloxegol or a pharmaceutically acceptable salt thereof by conventional process disclosed in the prior art or as described in the present application.

The treatment of 3-O-MEM Naloxol salt with a base is performed in presence of solvent. The solvent includes but are not limited to water, hydrocarbon, halogenated solvents and the like. The base is selected from inorganic base or organic base, which are defined above. After completion of reaction, the reaction mixture contained 3-O-MEM Naloxol free base is concentrated and reacted with naloxegol side chain of formula A:

Formula A wherein X is leaving group such as mesyl, tosyl, halo, nosyl
to provide 3-O-MEM Naloxegol.

In another aspect, the present invention provides a process for the purification of 3-O-MEM naloxegol having purity greater than or equal to 95.5%, which comprises:
i) treating 3-O-MEM naloxegol with acid to provide acid addition salt of 3-O-MEM naloxegol;
ii) optionally isolating the acid addition salt of step (i);
iii) treating the acid addition salt of 3-O-MEM naloxegol with a base to provide 3-O-MEM naloxegol;
iv) optionally, isolating 3-O-MEM naloxegol.

The 3-O-MEM naloxegol is treated with an acid such as inorganic or organic acid, which are defined above, especially the acid is oxalic acid. The solution of acid addition salt is washed with a solvent to remove impurities, which is further treated with a base. The base used to get pH of about 7.5 to 9.0 is selected from inorganic base or organic base, as defined above. The base particularly is selected from inorganic base i.e. sodium carbonate to convert oxalate salt to free base of 3-O-MEM naloxegol, which may be used to prepare Naloxegol or it may be isolated as solid.

In an embodiment, the present invention provides 3-O-MEM naloxegol oxalate, which may be formed as in-situ.

The resultant 3-O-MEM naloxegol is deprotected with an acid, which is selected from inorganic or organic acid or source thereof. The acid may be dry acid such as hydrochloric acid, trifluoro acetic acid or para toluene sulfonic acid, which may be dissolved in a solvent and used for deprotection. The deprotection step may be carried out in presence of antioxidant additive such as butylated hydroxytoluene (BHT) and in presence of solvent such as water, organic solvent such as alcohol, halogenated solvent, ester; or combination thereof. Preferably, the acid is source of acid i.e. hydrogen chloride in ethyl acetate. The resultant reaction mixture then subjected to pH adjustment of 8 to 9 with a base, preferably inorganic base, to provide Naloxegol free base.

In another aspect, the present invention provides a process for the purification of Naloxegol or salt thereof, which comprises:
i) treating Naloxegol with an acid to provide acid addition salt of naloxegol;
ii) optionally, isolating the acid addition salt of Naloxegol;
iii) treating the acid addition salt of Naloxegol with a base to provide pure Naloxegol or salt thereof.

The Naloxegol is treated with an acid such as inorganic acid to obtain acid addition salt of naloxegol. The inorganic acid is selected from hydrochloric acid, hydrobromic acid, sulfuric acid, and the like. In an embodiment, the present invention provides Naloxegol hydrobromide.

The acid addition salt of Naloxegol is then subjected for pH adjustment of the reaction mixture to 7 to 9.5 with a base to obtain Naloxegol free base in pure form. The inventors of the present invention found the difference in solubility of impurities and Naloxegol base at different pH and identified selective pH to obtain Naloxegol free base in pure form. The base is selected from sodium hydroxide, sodium carbonate, sodium bicarbonate, potassium hydroxide, potassium carbonate and the like.

The resultant pure Naloxegol further converted to oxalate salt of Naloxegol. The naloxegol is reacted with an oxalic acid in presence of a solvent or mixture of solvent selected from ether or ketone or alcohol.

In an embodiment, the process for preparation of Naloxegol oxalate, comprises:
a) providing a solution of Naloxegol in methyl tert-butyl ether;
b) diluting the solution of step a) with n-propyl alcohol;
c) adding oxalic acid solution in n-propanol and methyl tert-butyl ether or mixtures thereof;
d) optionally, seeding with naloxegol oxalate; and
e) isolating Naloxegol oxalate from step c) or step d).

In another aspect of the present invention, there is provided a process for the preparation of compound of formula A:

Formula A wherein X is leaving group such as mesyl, tosyl, halo, nosyl
which comprises:
a) condensation of triethyleneglycol monomethylether monomesylate with tetraethylene glycolmonobenzyl ether to provide heptaethylene glycol benzyl methyl ether;
b) convertion of the heptaethylene glycol benzyl methyl ether to compound of formula A.

The reaction of triethyleneglycol monomethylether monomesylate or monotosylate with tetraethylene glycol-monobenzyl ether is performed in presence of a base, which is selected from inorganic base or organic base at a temperature of about 0° C. to about 50° C. The reaction may be conducted in presence of a solvent such as water, alcohol, ether, aprotic polar solvents, hydrocarbon, nitrile, dimethylsulfoxide and the like. After completion of the reaction, the reaction mixture is washed with hydrocarbon, preferably, with cyclohexane.

The resultant heptaethylene glycol benzyl methyl ether, further, converted to naloxegol side chain of formula A. The heptaethylene glycol benzyl methyl ether may be treated with an acid to obtain heptaethylene glycol monomethyl ether, which may be further reacted with alkyl/aryl sulfonyl derivative such as methane sulfonyl chloride, toluene sulfonyl chloride, nosyl chloride and the like, or reacted with halogenating agent such as tetra-n-butylammonium chloride, tetra-n-butylammonium bromide and the like (or) both one after another to obtain Naloxegol side chain of Formula A.

In an embodiment, the compound of Formula A is 22-bromo-2,5,8,11,14,17,20-heptaoxadocosane. The resultant compound of 22-bromo heptaoxadocosane has purity greater than or equal to 99.7% by HPLC.

The overall process of the present invention is depicted in the following scheme:

The invention is illustrated with the following examples, which are provided by way of illustration only and should not be construed to limit the scope of the invention.

EXAMPLE 1

Preparation of Amorphous Form Naloxegol Oxalate

Naloxegol oxalate (10 g) was dissolved in purified water (180 ml) and to it Povidone k-30 (10 g) was added at 20-30° C. and was stirred to get solution. This solution was filtered through hyflo bed to get clear filtrate. The resulting solution was subjected to lyophilization after freezing at −40° C. to afford white solid (19.8 g). The XPRD analysis shows the product is amorphous. Water content is 1.8% w/w. Residual solvent by GC: methyl t-butylether: 146 ppm, n-propanol: 133 ppm. Purity: 99.52% by HPLC; Impurities: 0.04% (3-O-MEM αNaloxegol), 0.05% (PEG-5 naloxol), 0.33% (PEG-6 naloxol), and 0.06% (oxidative dimer).

EXAMPLE 2

Preparation of Amorphous Form Naloxegol Oxalate

A mixture of Naloxegol Base (2 g, HPLC purity>99.5%), Oxalic acid (0.28 g) and Povidone K 30 (1.2 g) were In yet another embodiment of the present invention, Naloxegol oxalate prepared according to present invention is converted to its pharmaceutical composition, together with one or more pharmaceutically acceptable excipients.

dissolved in a mixture of acetone (188 ml) and methanol (12 ml). This solution was filtered through hyflo bed to get clear filtrate, which was subjected to spray drying on BÜCHI mini spray dryer B-290 using inlet temperature 80° C., Aspiration 60%. The resultant solid was dried at 32-37° C. under reduced pressure (≤20 mm Hg) till constant weight to get titled compound (2.48 g).

The XPRD analysis showed that the product is amorphous.

Residual solvent by GC: Acetone: Not detected; Methanol: 75 ppm.

EXAMPLE 3

Preparation of 3-O-MEM Naloxone

N,N'-Diisopropylethylamine (21.4 g, 166 mmol) was added slowly to a solution of Naloxone hydrochloride dihydrate (50 g, 125 mmol) in dichloromethane (350 ml) at 15-20° C. Purified water (110 ml) added and biphasic solution was stirred. The layers were separated, and the aqueous layer was extracted with dichloromethane. The organic layers were combined and concentrated by distillation under reduced pressure at a temperature less than 40° C. till volume reaches to ~200 ml. and the dichloromethane solution gets dehydrated and dry. Diisopropylethylamine (42 g, 325 mmol) was added to the dichloromethane solution at 4-10° C. Thereafter, solution of MEM Chloride in dichloromethane [36 g, 289 mmol MEM chloride in 100 ml dichloromethane] over 55-65 min at 4-10° C. After reaction completion, purified water was added and biphasic solution was stirred. The layers were separated, and the aqueous layer was extracted with dichloromethane. Two organic layers were combined and the combined extract was washed with aqueous sodium hydroxide solution to remove the unreacted Naloxone. The dichloromethane extract was concentrated to an oily residue. Last traces of dichloromethane were removed by co-distilling with small amount of cyclohexane. The residue was stirred for 6 h with cyclohexane (400 ml) at about 16° C. to complete the precipitation of product, filtered and washed with cyclohexane (100 ml, 24° C.) and then dried at about 40° C. under reduced pressure till constant weight. Yield 97.4 g (94.6%). Melting range: 58-62° C. XRPD: FIG. 2. Purity (by HPLC): 99.85%.

EXAMPLE 4

Preparation of 3-O-MEM Naloxol α-epimer

Lithium tri-tert-butoxy aluminium hydride (LTBA, 19.93 g, 78.35 mmol) was added to toluene at 0-10° C. 3-O-MEM Naloxone (~200 ml, prepared by dissolving 25 g, 3-O-MEM Naloxone in a mixture of 187 ml toluene and 1 g, 2-Methoxyethanol) was added slowly drop-wise to the above obtained pre-cooled suspension of Lithium tri-tert-butoxy aluminium hydride in toluene at 0-10° C. After addition, temperature of reaction mass was raised to 20-30° C. and reaction mass was stirred for 1 h. The reaction was then stopped by adding ethyl acetate (2.5 ml) to the reaction mass at 5-10° C. Further, aqueous ammonium sulphate solution (10 g ammonium sulphate dissolved in 15 ml DM water) was added to the reaction mass at 5-10° C. and stirred for 10 minutes. The reaction mixture was treated with hyflo at 20-30° C., filtered through thin hyflo bed and washed with toluene. Toluene layer was separated and washed with DM water. The solvents were removed using rotary evaporator at temperature less than 60° C. to give viscous oily liquid (25.1 g, 100% isolated yield).

HPLC analysis indicated that 3-O-MEM Naloxol α-epimer is about 99.4% and 3-O-MEM Naloxol β-epimer is about 0.3%.

EXAMPLE 5

Preparation of 3-O-MEM α-Naloxol Oxalate Salt

3-O-MEM α-Naloxol (5 g) prepared in above example 4 was dissolved in n-propanol (20 ml) at 20-30° C. under nitrogen atmosphere. Oxalic acid (anhydrous) (1.07 g, 11.88 mmol) dissolved in n-propanol (10 ml) was added slowly drop-wise to the above at 20-30° C. and stirred for 30 minutes. Further methyl t-butyl ether (30 ml) was added slowly drop-wise to the above at 20-30° C. Oxalate salt precipitated out during addition, which was stirred for 90 minutes at 20-30° C. Product was filtered under nitrogen atmosphere and washed with Methyl t-Butyl ether (20 ml) and dried under vacuum at 20-25° C. to afford white solid (5.02 g).

XRPD shown as FIG. 3.

Purity: 99.58% by HPLC; 0.05% (β-3-O-MEM naloxol), 0.04 (6-alpha Naloxol).

Title compound was also prepared by using ethanol instead of n-propanol for the dissolution of 3-O-MEM α-Naloxol, and MTBE instead of n-propanol for the dissolution of oxalic acid.

Title compound was also be prepared by using 2-propanol (instead of n-propanol/MTBE).

EXAMPLE 6

Preparation of Oxalate Salt

3-O-MEM α-Naloxol (5 g) prepared in above example 4 was dissolved in 2-propanol (35 ml) at 20-30° C. under nitrogen atmosphere. Oxalic acid (11.66 mmol) was added to the above reaction mass at 20-30° C. Reaction mass was heated to 60-65° C. to get clear solution. Thereafter reaction mass was slowly cooled to 20-30° C. and stirred at same temperature for 30 minutes. Oxalate salt precipitated which was diluted by adding ethyl acetate and further stirred at 20-30° C. for 1 h. Product was filtered under nitrogen atmosphere and washed with mixture of ethyl acetate and 2-propanol and dried under vacuum at 20-25° C. to afford white solid (4.4 g).

EXAMPLE 7

Preparation of Oxalate Salt

3-O-MEM α-Naloxol (5 g) prepared in above example 4 was dissolved in ethyl acetate (50 ml) at 20-30° C. under nitrogen atmosphere which was cooled to 10-15° C. Oxalic acid (1.28 g, 14.3 mmol) dissolved in ethyl acetate (25 ml) was added slowly drop-wise to the above at 10-15° C. Oxalate salt precipitated out during addition, which was stirred for 60 minutes at 10-15° C. Product was filtered under nitrogen atmosphere and washed with ethyl acetate (50 ml) and dried under vacuum at 20-25° C. to afford white solid (5.9 g).

EXAMPLE 8

Preparation of 3-O-MEM Naloxegol

Sodium carbonate (3.14 g) was dissolved in water (50 ml) and to this solution was added toluene (45 ml) and 3-O-MEM-α-Naloxol oxalate (10 g, 19.7 mmol) at 15-20° C. The resulting solution was stirred at 20-30° C. for 30 minutes, and the organic layer separated and aqueous layer was extracted with toluene. The combined organic layer was washed with water. Butylated hydroxy toluene (BHT) (0.4 g) was added to the organic layer and then concentrated at a temperature less than 60° C. till volume reaches to ~20 ml. In another reaction vessel sodium hydride (1.5 g, 64.6 mmol) was added into a mixture of DMF (4 ml) and toluene (16 ml) at 5-10° C. To this slurry was added diluted solution of 3-O-MEM-α-Naloxol base (~20 ml) diluted with DMF (2 ml) in 30 minutes and then stirred for 30 minutes under nitrogen atmosphere. Thereafter, added a solution of 22-Bromo-heptaoxadocosane (30 g, 74 mmol) in a mixture of toluene (24 ml) and DMF (12 ml) for 3-4 h at 8-16° C. After reaction completion, aqueous ammonium chloride (15% w/w, 100 ml) was added to the reaction mass and extracted with Toluene (70 ml). The combined organic extracts were washed with brine (30 ml). Thereafter washed organic layer diluted with purified water and then cooled to 15-20° C. This solution was acidified with aqueous oxalic acid solution (10% w/w) at 15-20° C. Organic layer separated and the aqueous layer was washed with dichloromethane. The resulting aqueous layer containing 3-O-MEM naloxegol oxalate salt was added dichloromethane (50 ml) followed by neutralization with aqueous sodium carbonate solution (20% w/w) and stirred for 20 minutes at 20-30° C. The organic layer was separated and the aqueous layer was extracted with dichloromethane. The combined organic layer was concentrated by distillation under reduced pressure to afford 3-O-MEM Naloxegol (13 g) as a pale yellow colour liquid.

Purity: 95.76% by HPLC; Impurities: 1.44 (3-O-MEM alpha Naloxol) and 0.83% (6,14-dialkylated 3-O-MEM Naloxegol).

Title compound was also prepared by using 22-OMs-heptaoxadocosane instead of 22-Bromo-heptaoxadocosane in a manner similar to that described above.

EXAMPLE 9

Preparation of Naloxegol Base

Hydrogen chloride (~6% w/w) solution in ethyl acetate (31 g, 51 mmol) was slowly added to the solution of 3-O-MEM Naloxegol (10 g, 13.5 m mol) in ethyl acetate (20 ml) containing Butylated hydroxy toluene (BHT) (0.1 g) at 10-15° C. and the mixture was stirred for ~90 min at 10-15° C. After reaction completion, purified water (50 ml) was added at 10-20° C. Organic layer was separated and the aqueous layer was washed with ethyl acetate (20 ml). The aqueous solution containing Naloxegol hydrochloride was neutralized by addition of aqueous sodium carbonate solution (20% w/w) and the product was extracted with dichloromethane (80 ml). The dichloromethane solution was concentrated by distillation under reduced pressure to get pale yellow colored viscous liquid/residue. The residue was diluted with purified water (30 ml) and then acidified by addition of aqueous hydrobromic acid solution (~20% w/w) at 10-20° C. The aq. solution containing product as hydrobromide salt is repeatedly washed with dichloromethane. The washed aqueous solution containing Naloxegol hydrobromide is neutralized with aq. sodium carbonate solution, extracted with dichloromethane, washed with water and then concentrated to afford Naloxegol (6.9 g) as a pale yellow colour viscous liquid.

EXAMPLE 10

Preparation of Naloxegol Oxalate

Naloxegol (5 g) was dissolved in MTBE (40 ml) and n-propanol (5 ml). The solution of Oxalic acid (0.7 g) prepared in MTBE (30 ml) and n-propanol (2 ml) was added slowly to the Naloxegol base solution. Naloxegol oxalate was precipitated during addition and product slurry was further stirred for about 3 hours. It was then cooled to 12-15° C. and further stirred for about 45 minutes. Product was filtered under nitrogen atmosphere and was washed with MTBE and dried under vacuum at 25-30° C. to afford white solid (5.0 g).

Purity: 98.58% by HPLC; Impurities: 0.03% (3-O-MEM-naloxegol), 0.05% (dialkyllated Naloxegol), 0.08% (β-epimer), 0.64% (PEG-8 Naloxegol), 0.37% (PEG-6 Naloxegol), 0.08% (PEG-5 naloxegol) and 0.07% (PEG-3 naloxegol).

EXAMPLE 11

Preparation of Naloxegol Side Chain

A). Preparation of Triethylene Glycol Monomethyl Ether Monomesylate:

Triethylene glycol monomethyl ether (200 g; 1.21 moles) was dissolved in methylene chloride (800 ml). To this solution added Triethylamine (148 g; 1.46 moles) and cooled to 0-5° C. The solution of methanesulfonyl chloride (167.4 g; 1.46 moles) prepared in methylene chloride (260 ml) was added slowly to the above solution and stirred for 1 hour at 20-30° C. The mixture was then cooled 5-10° C. and water (400 ml) was added. The layers were separated and the organic layer was washed with aq. NaHCO$_3$ solution followed by with water and then concentrated by distillation under reduced pressure to afford title compound (250 g).

Purity by GC: 98.58%; Impurities: PEG 3 monomethyl ether: 0.11%; PEG 2 dimesylate: 0.45% and PEG 3 monochloro monomethyl ether: 0.06%

B). Preparation of Tetraethylene Glycol Monobenzyl Ether:

Sodium hydroxide powder (47.5 g; 1.18 moles) was slowly added to tetraethylene glycol (460 g; 2.37 moles) at 20-25° C. Benzyl chloride (100 g; 0.79 moles) was added slowly to the mixture and stirred for 6 hours. Water (1 L) was added slowly and adjusted pH of the reaction to 9.5-10 with aq. HCl solution. The aqueous layer was extracted with cyclohexane to remove the tetraethyleneglycol dibenzylether. The aqueous layer again was extracted with toluene and washed the organic layer with aq. NaCl solution and then concentrated to afford titled compound (135 g).

HPLC purity: 99.15%; Impurities: PEG 3 monobenzyl ether: 0.09%; PEG 5 monobenzyl ether: 0.13% and PEG 4 dibenzyl ether: 0.21%.

C). Preparation of Heptaethylene Glycol Monomethyl Ether:

Potassium hydroxide (40 g; 0.71 moles) was added to THF (600 ml) and then added tetraethylene glycol monobenzyl ether (100 g; 0.352 moles), raised the temperature to 60-70° C. and stirred for 30 min. The solution of triethylene glycol monomethyl ether monomesylate (90 g; 0.371 moles) prepared in THF (100 ml) was added slowly to the above solution and stirred for 24 hours at reflux. The reaction mixture was concentrated under reduced pressure and added water. The concentrated aq. reaction mass was extracted with cyclohexane followed by toluene to remove the non polar impurities. The separated organic layer washed with aq. sodium chloride solution and then concentrated to afford heptaethyleneglycol monobenzyl monomethylether (120 g) as a reddish brown color residue (HPLC purity 96.2%).

The above concentrate mass was dissolved in ethanol and treated with carbon. To the filtrate conc.HCl (1.2 ml) was added and then taken the solution in an autoclave and 10% palladium on carbon paste (2.50 g, contains ~50% w/w water) was added and used 5-6 Kg/Cm2 hydrogen pressure for 4 hours. Sodium bicarbonate (3.6 g) was added to neutralize the hydrochloric acid, filtered through hyflo pad, washed the residue with ethanol. The combined ethanol filtrate was concentrated to yellow oily residue. The concentrated mass was dissolved in water and washed with ethyl acetate. Two layers were separated and the aqueous layer was again extracted with methylene chloride and washed organic layer with purified water and concentrated under reduced pressure to afford titled compound as a pale yellow liquid (54 g).

Purity by GC: 99.0%; Impurities: PEG 6 monomethyl ether: 0.24%; PEG 6 dimethyl ether:0.27%; PEG 5 monomethyl ether: 0.04%; PEG 8 monomethyl ether: 0.14%.

D) Preparation of 22-Bromo-2,5,8,11,14,17,20-heptaoxadocosane:

The above obtained compound (200 g; 0.588 moles) was dissolved in methylene chloride (700 ml) and cooled to 0-5° C. To this solution triethyl amine (92 g; 0.91 moles) was added and then solution of Methanesulfonyl chloride (84 g; 0.733 moles) prepared in methylene chloride (240 ml) was added slowly to the above solution and stirred for 30 min. The temperature was raised to 20-30° C. and stirred for 1 hour, and then cooled 5-10° C. The reaction mixture was diluted with dichloromethane, followed by water, organic layer was separated and washed with aq. sodium bicarbonate solution and with water, and then concentrated under reduced pressure to afford Heptaethylene glycol monomethylether monomesylate (240 g) as a yellow color liquid. The concentrated residue was dissolved in toluene (1000 ml) and added Tetra-n-butylammonium bromide (197 g; 0.611 moles) at 20-30° C. The reaction mass was heated to 80-85° C. and maintained for 2 hours. The mixture was cooled and water was added, the organic layer was separated, aq. solution was extracted with toluene. The combined organic layers were washed with aqueous sodium chloride solution and then concentrated the toluene layer under reduced pressure to afford titled compound as a pale yellow color liquid (190 g).

GC purity: 98-99%; Impurities: PEG 5 Monobromo Monomethyl Ether: 0.17%; PEG 6 Monobromo Monomethyl Ether: 0.25%; PEG 8 Monobromo Monomethyl ether: 0.18%; PEG7 Monochloro Monomethyl Ether: 0.5%.

We claim:

1. A solid dispersion of stable amorphous Naloxegol oxalate in a combination with Povidone K-30 in 1:1 w/w ratio and characterized by XRPD pattern of FIG. 1.

2. The solid dispersion as claimed in claim 1, wherein the amorphous solid dispersion having purity of about 99.5% by HPLC and broad diffraction (halo) in XRPD.

3. A process for the preparation solid dispersion of amorphous Naloxegol oxalate, which comprises:
   a) providing a solution of Naloxegol oxalate in water;
   b) adding Povidone K-30 in % w/w ratio 1:1; and
   c) lyophilizing the step b) and isolating stable amorphous solid dispersion of Naloxegol oxalate.

4. The process as claimed in claim 3, wherein the amorphous solid dispersion is characterized by XRPD pattern by FIG. 1.

5. The process as claimed in claim 3, wherein the amorphous solid dispersion has impurity content of 0.04% of 3-O-MEM α-naloxegol, 0.05% PEG-5 naloxol, 0.06% oxidative dimer.

* * * * *